(12) United States Patent
Stewart et al.

(10) Patent No.: US 8,702,703 B2
(45) Date of Patent: Apr. 22, 2014

(54) SUB-XIPHOID ABLATION CLAMP AND METHOD OF SUB-XIPHOID ABLATION

(75) Inventors: Mark T. Stewart, Lino Lakes, MN (US); Tom P. Daigle, Corcoran, MN (US); David E. Francischelli, Anoka, MN (US); John R. Liddicoat, Minneapolis, MN (US); Paul T. Rothstein, Elk River, MN (US); Steven F. Bolling, Ann Arbor, MN (US)

(73) Assignee: Medtronic, Inc., Minneapolis, MN (US)

( * ) Notice: Subject to any disclaimer, the term of this patent is extended or adjusted under 35 U.S.C. 154(b) by 931 days.

(21) Appl. No.: 12/769,345

(22) Filed: Apr. 28, 2010

(65) Prior Publication Data

US 2010/0292749 A1    Nov. 18, 2010

Related U.S. Application Data

(60) Provisional application No. 61/177,533, filed on May 12, 2009.

(51) Int. Cl.
   *A61B 18/18* (2006.01)

(52) U.S. Cl.
   USPC ............... 606/51; 606/45; 606/50; 606/52

(58) Field of Classification Search
   USPC ..................................... 606/50–52
   See application file for complete search history.

(56) References Cited

U.S. PATENT DOCUMENTS

| | | | |
|---|---|---|---|
| 4,784,133 A | 11/1988 | Mackin | |
| 5,147,373 A | 9/1992 | Ferzli | |
| 5,674,220 A | 10/1997 | Fox et al. | |
| 5,916,214 A | 6/1999 | Cosio et al. | |
| 5,951,549 A | 9/1999 | Richardson et al. | |
| 6,161,543 A | 12/2000 | Cox et al. | |
| 6,237,605 B1 | 5/2001 | Vaska et al. | |
| 6,443,944 B1 | 9/2002 | Doshi et al. | |
| 6,478,794 B1 | 11/2002 | Trapp et al. | |
| 6,572,615 B2 | 6/2003 | Schulze et al. | |
| 6,610,060 B2 | 8/2003 | Mulier et al. | |
| 6,613,048 B2 | 9/2003 | Mulier et al. | |
| 6,616,661 B2 | 9/2003 | Wellman et al. | |
| 6,697,240 B2 | 2/2004 | Nelson et al. | |
| 6,770,072 B1 | 8/2004 | Truckai et al. | |
| 6,899,711 B2 | 5/2005 | Stewart et al. | |

(Continued)

OTHER PUBLICATIONS

PCT International Search Report (PCT/US2010/033719) dated Aug. 26, 2010 (4 pages).

*Primary Examiner* — Linda Dvorak
*Assistant Examiner* — Jaymi Della

(57) ABSTRACT

Device and method for sub-xiphoid ablation of patient tissue. A sub-xiphoid access clamp has a handle, an elongate neck coupled to the handle and first and second opposing jaws. The first and second opposing jaws have first and second opposing relief segments being generally co-planar and concave with respect to one another to form a void therebetween, and first and second opposing elongate ablation elements positioned along the first and second opposing jaws and distal of the first and second opposing relief segments relative to the handle. The first and second opposing jaws are articulate between a closed position and an open position to admit, at least in part, a second portion of tissue of the patient within the void created by the first and second opposing relief segments while the first portion of tissue is positioned between the first and second ablation elements in the closed position.

8 Claims, 14 Drawing Sheets

(56) References Cited

U.S. PATENT DOCUMENTS

| | | |
|---|---|---|
| 7,166,106 B2 | 1/2007 | Bartel et al. |
| 7,297,145 B2 | 11/2007 | Woloszko et al. |
| 7,470,272 B2 | 12/2008 | Mulier et al. |
| 7,487,780 B2 | 2/2009 | Hooven |
| 7,582,086 B2 | 9/2009 | Privitera et al. |
| 7,678,111 B2 | 3/2010 | Mulier et al. |
| 7,717,912 B2 | 5/2010 | Woloszko et al. |
| 7,758,576 B2 | 7/2010 | Rothstein et al. |
| 7,758,580 B2 | 7/2010 | Rothstein et al. |
| 7,951,147 B2 | 5/2011 | Privitera et al. |
| 2002/0091382 A1 | 7/2002 | Hooven |
| 2003/0040745 A1 | 2/2003 | Frazier et al. |
| 2003/0091383 A1* | 5/2003 | Conway ........................ 403/348 |
| 2003/0114850 A1 | 6/2003 | McClurken et al. |
| 2004/0044335 A1 | 3/2004 | de la Torre et al. |
| 2004/0073210 A1 | 4/2004 | Taniguchi et al. |
| 2004/0138522 A1* | 7/2004 | Haarstad et al. ................ 600/37 |
| 2004/0216748 A1 | 11/2004 | Chin |
| 2005/0090817 A1 | 4/2005 | Phan |
| 2005/0113821 A1 | 5/2005 | Pendekanti et al. |
| 2005/0131392 A1 | 6/2005 | Chu et al. |
| 2006/0020263 A1 | 1/2006 | Rothstein et al. |
| 2006/0084974 A1 | 4/2006 | Privitera et al. |
| 2006/0167449 A1 | 7/2006 | Mulier et al. |
| 2007/0203484 A1* | 8/2007 | Kim et al. ........................ 606/41 |
| 2008/0114354 A1 | 5/2008 | Whayne et al. |

* cited by examiner

SUB-XIPHOID ABLATION CLAMP AND METHOD OF SUB-XIPHOID ABLATION

PRIORITY

This application claims the benefit of U.S. Provisional Application No. 61/177,533, filed on May 12, 2009, entitled "TISSUE ABLATION CLAMP AND METHOD".

BACKGROUND

Atrial fibrillation is a common cardiac condition in which irregular heart beats cause a decrease in the efficiency of the heart, sometimes due to variances in the electrical conduction system of the heart. In some circumstances, atrial fibrillation poses no immediate threat to the health of the individual suffering from the condition, but may, over time, result in conditions adverse to the health of the patient, including heart failure and stroke. In the case of many individuals suffering from atrial fibrillation, however, symptoms affecting the patient's quality of life may occur immediately with the onset of the condition, including lack of energy, fainting and heart palpitations.

In some circumstances, atrial fibrillation may be treated through the application of defibrillation shocks. In cases of persistent atrial fibrillation, however, surgery may be required. A surgical procedure originally developed to treat atrial fibrillation is known as a "MAZE" procedure where the atria are surgically cut along specific lines and sutured back together. While possibly effective, the MAZE procedure tends to be complex and may require highly invasive access to the thorax. In order to reduce the need to open the atria, thermal ablation tools were developed to produce lines of inactive heart wall that mimic the MAZE procedure. Such ablation tools commonly utilize radio frequency (RF) ablation devices to ablate and isolate tissue which may be responsible for the improper electrical conduction that causes atrial fibrillation. One such location of tissue which may be responsible for improper electrical conduction is at the junction of the pulmonary veins with the left atrium where spontaneous triggers for initiation of atrial fibrillation have been found. Patients who suffer from a paroxysmal form of atrial fibrillation experience short, self terminating episodes of atrial fibrillation. "Lone" atrial fibrillation occurs in patients who have either few or no other significant cardiac diseases.

Access to the left pulmonary veins by an inferior approach may be relatively free from interference. However, ablation around the right pulmonary veins may be relatively more complicated due to the presence of the superior and inferior vena cava as well as by pericardial tissue called a pericardial reflection. Pericardial reflections stretch from the right pulmonary veins to the superior vena cava, from the right pulmonary veins to the inferior vena cava, and the right superior pulmonary vein the left superior pulmonary vein. These pericardial reflections may effectively block any ability to surround the right pulmonary veins so as to ablate tissue in and around the right pulmonary veins without first dissecting at least one, and generally two, of the pericardial reflections to physically permit access to an ablation device. Pericardial reflection dissection may be undesirable under minimally invasive access. A procedure requiring dissection of the pericardial reflections may significantly increase the time required to do the overall procedure and increase the risk of unintended tearing or perforation of the heart or extracardiac structures. Moreover, while the right pulmonary veins may be accessible from the inferior side of the heart, by a sub-xiphoid access procedure, the presence of the inferior vena cava may make the ability to clamp an ablation device on the right pulmonary veins difficult or impossible without constricting the flow of blood through the inferior vena cava.

SUMMARY

A sub-xiphoid ablation clamp has been developed that allows for the ablation of tissue on and around the right pulmonary veins in a sub-xiphoid access procedure that may not require the dissection of any pericardial reflection and that may not obstruct blood flow through the inferior vena cava. In particular, a sub-xiphoid ablation clamp at the end of a malleable neck has ablation members arrayed along the jaws of the sub-xiphoid ablation clamp. One of the jaws may pass to the right of the inferior vena cava, with the other jaw passing to the left, until the ablation elements are positioned proximate the tissue to be ablated. A relief segment on each of the jaws creates a space such that when the jaws are clamped down for the ablation procedure a void is created in the jaws into which the inferior vena cava may fit with at least sufficiently little distortion to prevent a significant occlusion of blood through the vein. In an embodiment, the sub-xiphoid ablation clamp allows a unique method of clamping on the right pulmonary veins and also allows clamping on the left pulmonary veins without the need for dissection of any pericardial reflections.

In an embodiment, a sub-xiphoid ablation clamp for ablating a first portion of tissue of a patient has a handle, an elongate neck operatively coupled to the handle and first and second opposing jaws. The first and second opposing jaws have first and second opposing relief segments coupled to the elongate neck and being generally co-planar and concave with respect to one another to form a void therebetween and first and second opposing elongate ablation elements positioned along the first and second opposing jaws and distal of the first and second opposing relief segments relative to the handle, respectively, and configured to ablate the first portion of tissue positioned therebetween. The first and second opposing jaws are articulate between a closed position and an open position to admit, at least in part, a second portion of tissue of the patient within the void created by the first and second opposing relief segments while the first portion of tissue is positioned between the first and second ablation elements in the closed position.

In an embodiment, the first and second opposing jaws articulate proximal of the first and second relief portions relative to the handle.

In an embodiment, the first and second opposing jaws articulate distal of the first and second relief portions relative to the handle.

In an embodiment, the first and second opposing jaws each further comprise a first and second atraumatic tip, respectively.

In an embodiment, the first and second atraumatic tips are spherical.

In an embodiment, the first and second elongate ablation elements are positioned, at least in part, on the first and second atraumatic tips, respectively.

In an embodiment, the sub-xiphoid ablation clamp further has an imaging member associated with the first and second jaws.

In an embodiment, the imaging member has a light source.

In an embodiment, the first and second opposing jaws actuate along a plane defined by a plane formed by the first and second relief segments.

In an embodiment, the first and second opposing ablation elements articulate distal of the relief segments along a plane generally orthogonal to the plane defined by the first and second relief segments.

In an embodiment, a plane of the first and second opposing ablation elements fixedly form a generally orthogonal angle relative to the plane of the first and second relief segments.

In an embodiment, at least one of the first and second jaws further has an electrode.

In an embodiment, the electrode is configured to perform at least one of pacing a heart of the patient and sensing a cardiac signal of the heart of the patient.

In an embodiment, the first portion of tissue is a right pulmonary vein of the patient and the second portion of tissue is an inferior vena cava of the patient.

In an embodiment, the first and second relief segments are sized to admit the inferior vena cava in the void formed by the first and second relief segments without substantially restricting blood flow through the inferior vena cava.

In an embodiment, method of sub-xiphoid ablation of a first vein of a heart of a patient uses a sub-xiphoid ablation clamp having first and second opposing jaws comprising first and second opposing relief segments being generally co-planar and concave with respect to one another to form a void therebetween and first and second opposing elongate ablation elements positioned along the first and second opposing jaws and distal of the first and second opposing relief segments relative to a handle, respectively, and configured to ablate the first vein positioned therebetween, wherein the first and second opposing jaws are articulable. The method has the steps of approaching the heart with the jaws of the sub-xiphoid ablation clamp from a sub-xiphoid direction, positioning a second vein within the void formed by the first and second relief segments and the first vein between the first and second opposing ablation elements, clamping the first vein between the first and second opposing ablation elements while maintaining blood flow through the second vein and delivering ablation energy to the first vein.

In an embodiment, the first vein is a right pulmonary vein and the second vein is an inferior vena cava.

In an embodiment, the sub-xiphoid ablation clamp further has an electrode positioned on the sub-xiphoid ablation clamp to contact tissue of the patient when the ablation elements are in contact with the tissue of the patient, and the method further has the step of delivering pacing energy to the heart of the patient to generate a result.

In an embodiment, the delivering ablation energy step is based, at least in part, on the result.

In an embodiment, the sub-xiphoid ablation clamp further has an electrode positioned on the sub-xiphoid ablation clamp to contact tissue of the patient when the ablation elements are in contact with the tissue of the patient, and the method further has the step of sensing a cardiac signal from the heart of the patient.

In an embodiment, the delivering ablation energy step is based, at least in part, on the cardiac signal sensed from the heart.

In an embodiment, the sub-xiphoid ablation clamp further has an imaging member generating an output, and at least one of the approaching step and positioning step are based, at least in part, on the output.

FIGURES

DETAILED DESCRIPTION

The entire content of provisional U.S. Provisional Application Ser. No. 61/177,533, filed May 12, 2009 is hereby incorporated by reference.

Figure 1:
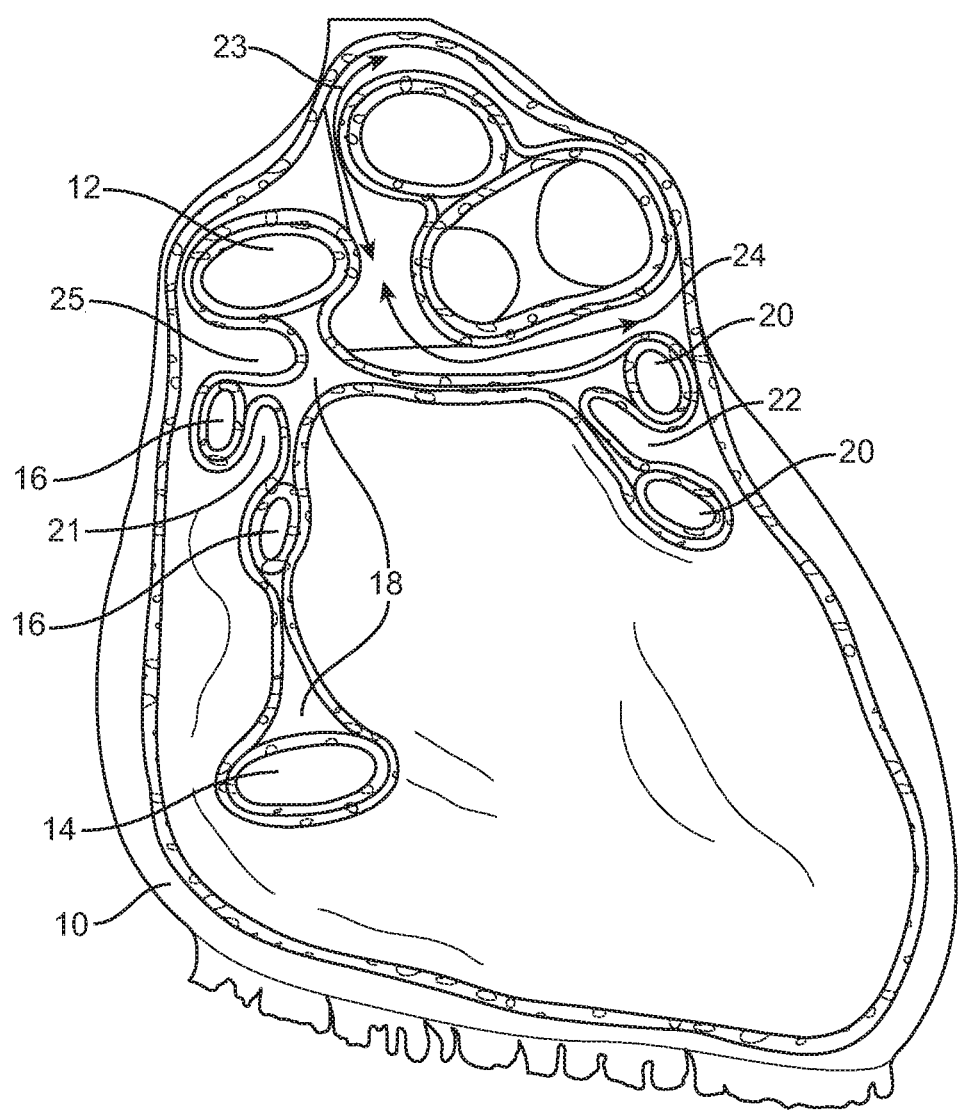
FIG. 1 is a view of the pericardial recess in which the posterior aspect of a human heart lays, also seen are the great vessels that attach to the heart.

FIG. 1 shows a posterior view of a diagram of the tissues and great vessels extending posteriorly from the cast formed by the pericardial sac of the human heart 10. Superior vena cava 12 and inferior vena cava 14 deliver de-oxygenated blood to the heart from the upper and lower regions of the body, respectively. The two right pulmonary veins 16 and two left pulmonary veins 20, deliver oxygenated blood from the lungs to the left atrium. Pericardial reflections 18 extend between superior vena cava 12, inferior vena cava 14, right pulmonary veins 16 and left pulmonary veins 20. A right pulmonic vein recess 21 is between the right pulmonary veins 16, and a left pulmonic vein recess 22 is between the left pulmonary veins 20. Superior sinus 23, transverse sinus 24, and postcaval recess 25 are also identified.

Figure 2A:
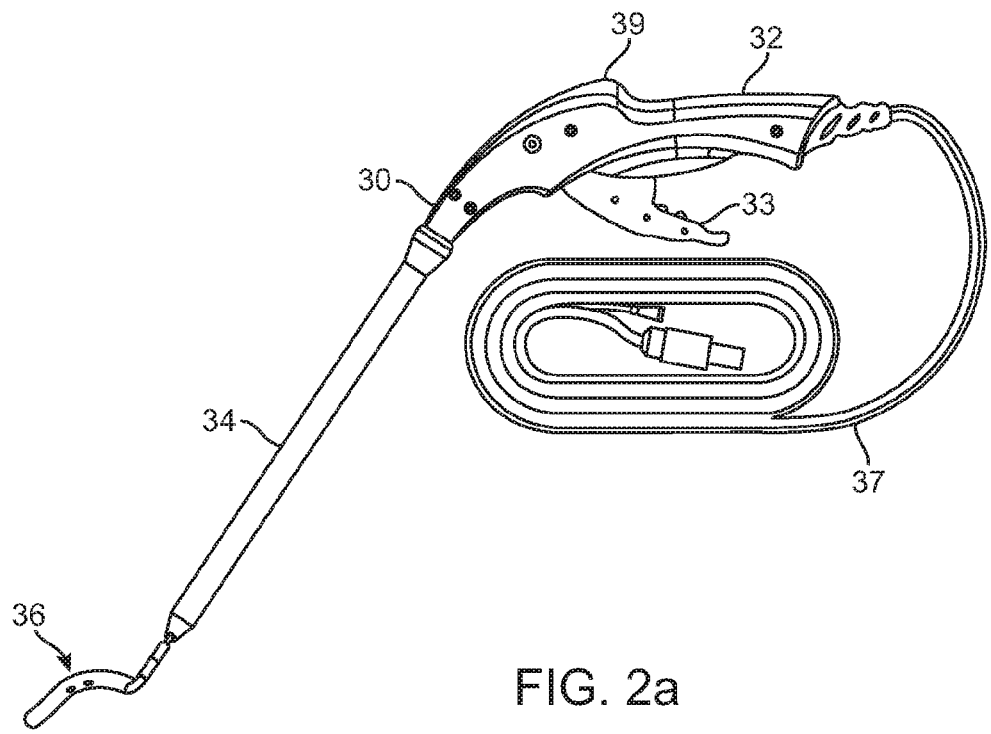
FIGS. 2a and 2b are side and top views of a sub-xiphoid ablation clamp.
Figure 2B:
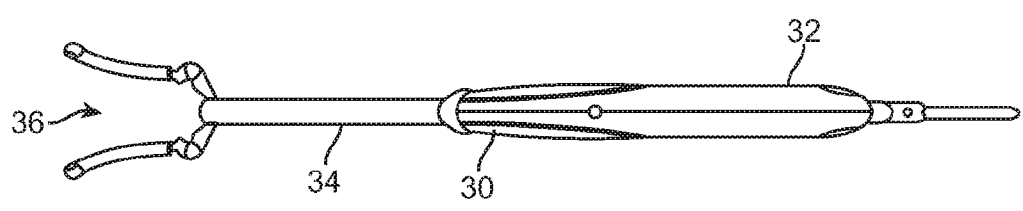

FIGS. 2a and 2b show a side view and a top view, respectively, of an embodiment of sub-xiphoid ablation clamp 30 that permits a sub-xiphoid approach to access heart 10, and right pulmonary veins 16 in particular, without dissecting pericardial reflections 16 or harmfully occluding or obstructing the blood flow through inferior vena cava 14. Handle 32 allows for grasping, manipulation and use of sub-xiphoid ablation clamp 30 by a medical professional. Grasping trigger 33 provides at least some control and manipulation of sub-xiphoid ablation clamp 30, including, in various embodiments, clamping and delivery of ablation energy. Neck 34 may be elongate and malleable to assist in the positioning of sub-xiphoid ablation clamp 30 in proximity of heart 10. In an embodiment, a flexible neck 34 may be a malleable corrugated tube. In an embodiment a tube having a wall thickness of approximately 0.016 inches (0.0406 centimeters) may provide torquability while giving neck 34 malleability to be re-shaped. Jaw structure 36 is positioned at the distal end of neck 34, and may include opposing jaws, ablation members, atraumatic tips and opposing relief sections to create a space to allow jaw structure to circumscribe or not fully clamp and occlude inferior vena cava 14. Cord 37 is configured to be coupled to a source of ablation energy and a source of conductive fluid.

In various embodiments, neck 34 is selected based on patient physiology and may be of a length adequate to perform a sub-xiphoid approach. In certain embodiments, the length of neck 34 is from ten (10) centimeters to thirty-five (35) centimeters. In an embodiment, neck is approximately 22.86 centimeters long. In an alternative embodiment, neck is approximately 15.8 centimeters long. In various embodiments neck 34 has a width from one-half (0.5) centimeter to two (2) centimeters. In an embodiment, neck 34 has a width of approximately 1.27 centimeters.

In various embodiments, sub-xiphoid ablation clamp 30 is angled at various locations in order to provide improved access for sub-xiphoid ablation procedures. In various embodiments, a handle 34 is curved such that a primary axis of neck 34 is angled from approximately fifty (50) degrees to approximately sixty-five (65) degrees relative to a line tangent to apex 39 of handle 32. In an embodiment, the angle of neck 34 to the line tangent to apex 39 is approximately fifty-seven (57) degrees.

Figure 3A:
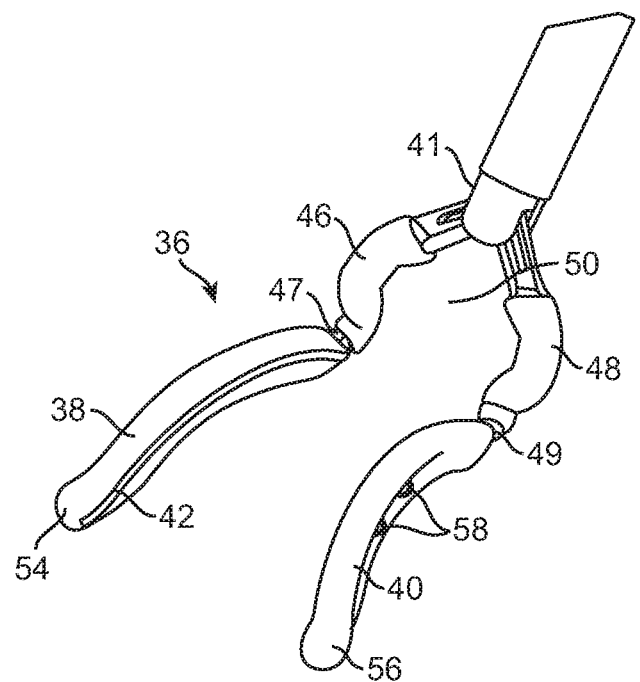
FIGS. 3a, 3b, 3c and 3d are various views of a jaw structure of the sub-xiphoid ablation clamp.
Figure 3B:
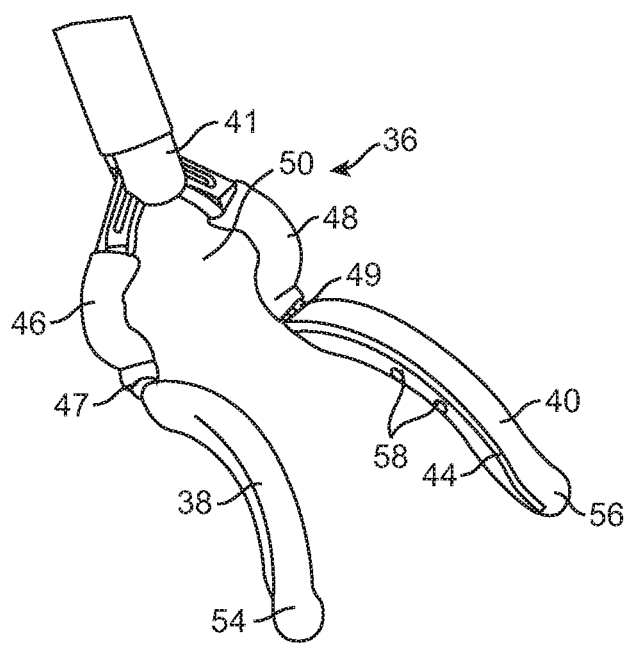
Figure 3C:
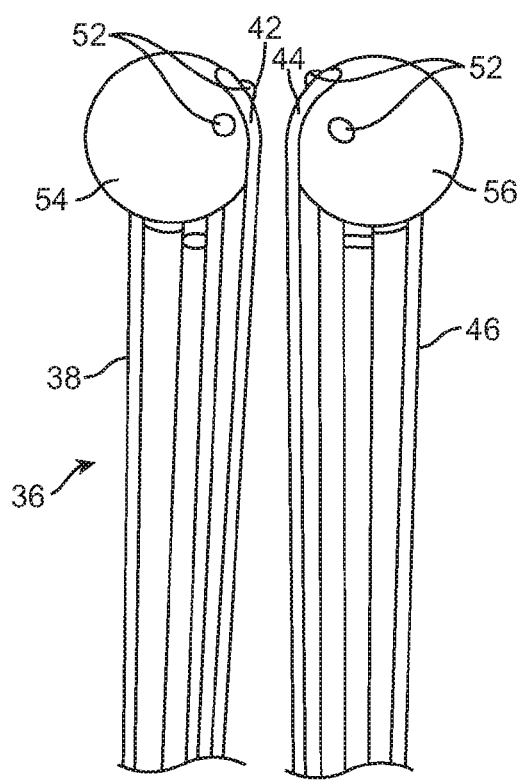
Figure 3D:
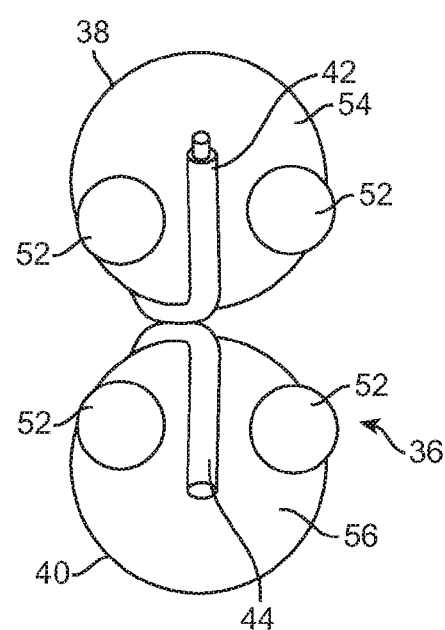

FIG. 3a shows an embodiment of jaw structure 36, which is also illustrated in FIG. 3b in a complementary side view, in FIG. 3c in a second, close-up side view and FIG. 3d in an end view. First elongate jaw 38 and second elongate jaw 40 oppose each other and are coupled to pivot 41 about which each may be actuated from a closed position to an open position and vice versa. First jaw 38 and second jaw 40 have first ablation member 42 and second ablation member 44, respectively. In the illustrated embodiment, first ablation member 42 and second ablation member 44 (obscured in FIG. 3a) provide for bipolar electrical ablation of tissue that has been interposed between the ablation members 42, 44. Opposing relief segments 46 and 48, coupled to jaws 38, 40 at junctions 47, 49, respectively, create and define void 50 which may be sized to circumscribe inferior vena cava 14.

In various embodiments, ablation members 42, 44 may be electrodes. Such electrodes may be designed for creating transmural lesions on heart 10 and may also be designed to achieve visible surface lesions. Jaws 38, 40 may be covered by sheaths that consist of silicone, polyvinylchloride, polyurethane, or similar materials. Alternatively, jaws 38, 40 may be coated with rigid polymeric materials such as polycarbonate or acrylonitrile butadiene styrene (ABS) plastic. In various embodiments, jaws 38, 40 are from approximately five (5) centimeters to approximately fifteen (15) centimeters in length. In an embodiment, jaws 38, 40 are approximately eleven (11) centimeters. The electrically active parts of ablation members 42, 44 may be stainless steel hypo-tubes contained within lengths of porous polymer such as sintered ultra-high molecular weight polyethylene. The ablation members 42, 44 may be mounted in seating areas located on the clamping surface of jaws 38 and 40.

Figure 5:
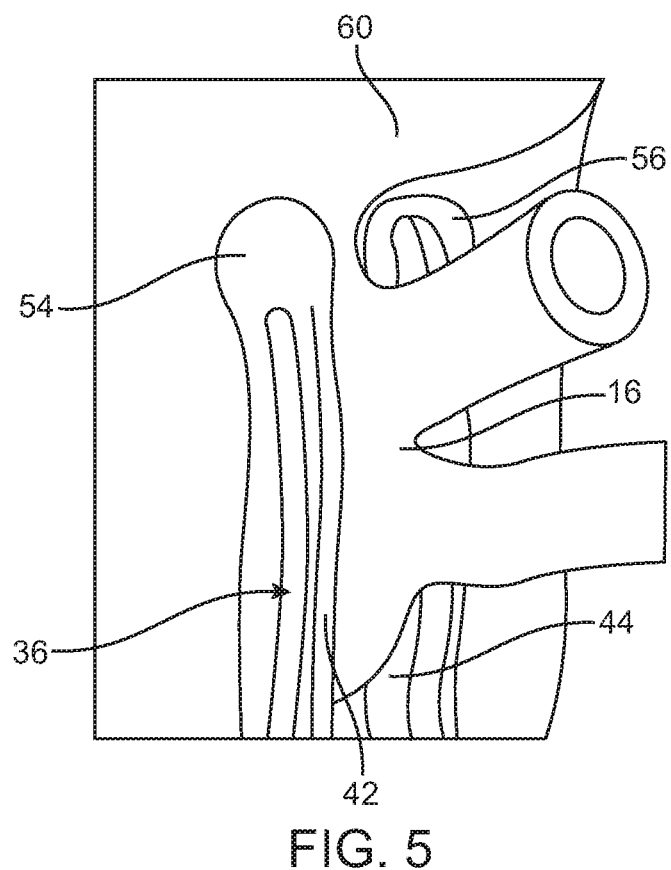
FIG. 5 is a close-up image of the sub-xiphoid ablation clamp being used as in FIG. 4.

In various embodiments, the length of ablation members 42, 44 may be from approximately three (3) centimeters long to approximately eight (8) centimeters long. In such embodiments, ablation members 42, 44 may be selected to extend proximate atraumatic tip 54 (FIG. 5). The length may be selectable on the basis of the length of the lesion desired to be created on heart 10. In various embodiments, a kit may be provided with multiple jaw structures 36 with different length ablation elements 42, 44 which may be selected and utilized based on the particular needs of the patient. In various embodiments ablation elements 42, 44 are between five (5) and seven (7) centimeters long. In an embodiment, jaw structure 36 has ablation elements 42, 44 having a length of six (6) centimeters. In an alternative embodiment, ablation elements 42, 44 are GEMINI® devices manufactured by Medtronic, Inc., Minneapolis, Minn. and have a length of 6.3 centimeters. In an embodiment, ablation members 42, 44 are formed from platinum flat wire wound into coils.

In an embodiment, relief segments 46, 48 define a length from approximately one (1) centimeter to approximately four (4) centimeters from neck 34 to jaws 38, 40, and may be selected based on the physiology of heart 10. In particular, relief segments may be selected based, at least in part, on a thickness of inferior vena cava 14 and a distance from inferior vena cava 14 and right pulmonary veins 16. In an embodiment, relief segments define a length of approximately 2.5 centimeters. Relief segments 46, 48 may define void 50 having a width from 0.5 centimeters to two (2) centimeters when jaws 38, 40 are in a closed position. In an embodiment, relief segments 46, 48 define void 50 having a width of approximately one (1) centimeter.

In an embodiment, jaws 38, 40 are curved having a radius of curvature from approximately 2.0 centimeters to approximately six (6) centimeters. The radius of curvature of jaws 38, 40 may be selected based, at least in part, on a physiology of heart 10 and the nature of the lesion sought to be created. In an embodiment, the radius of curvature of jaws 38, 40 is approximately 4.3 centimeters.

In further embodiments, jaws 38, 40 define an angle relative to the primary axis of neck 34 and relief segments 46, 48. In various embodiments an angle between jaws 38, 40 and the primary axis of neck 34 is defined by the angle between the primary axis of neck 34 and a line tangent to jaws 38, 40 proximate junctions 47, 49. In various embodiments, the angle between the primary axis of neck 34 and jaws 38, 40 is between approximately ninety (90) degrees and approximately one hundred thirty-five (135) degrees. In such embodiments, the angle may be selected based, at least in part, on the anatomy of heart 10. In an embodiment, the angle between the primary axis of neck 34 and jaws 38, 40 is approximately ninety-six (96) degrees.

In various embodiments, jaws 38, 40 in a fully-open position define a width between tips 54, 56 from approximately 2.5 centimeters to approximately 7.5 centimeters. In such embodiments, the fully-open position may be selected based on a physiology of heart 10. In an embodiment, jaws 38, 40 in a fully-open position create a distance of approximately 5.6 centimeters between tips 54, 56.

Ports 52 may provide accessibility for various components which may be useful in utilizing sub-xiphoid ablation clamp 30. In various embodiments, electrodes may be placed in ports 52 for sensing ablation energy delivered or underlying activity of heart 10. Location members may also be positioned in ports 52. Such location members may include lights, such as light emitting diodes, which may illuminate the tissue around jaw structure 36. Such illumination may provide for both direct visual observation of patient tissue, or may backlight patient tissue interposed between port 52 and the user of sub-xiphoid ablation clamp 30. By backlighting, for instance, pericardial reflection 18, light emitting diodes may give a user an approximate idea of the location of jaw structure 36 relative to a desired location in heart 10. Alternative location members are also envisioned, such as radio frequency transponders, Hall-effect sensors, and other broadcasting members and mechanical means.

In various embodiments, ports 52 may form the terminus of a lumen or passage that leads back to handle 32. The lumen may allow for various devices to be advanced from the handle 32 to ports 52. Such devices may include electrogram recording catheters, ablation catheters, pig-tail catheters, or fiber-optic imaging conduits. In further embodiments, ports 52 may also contain one or more imaging devices such as charge coupled devices (CCDs) to allow viewing of the anatomy of the patient from the tip of the ablation jaws.

In a further embodiment, light emitting diodes may be positioned in ports 52. In an embodiment, one port 52 may incorporate a light emitting diode while another port 52 incorporates a light intensity sensing device such as a photoresister, photovoltaic device, photodiode, or other light measuring detector which may provide information regarding the intensity of light passing through tissue between the light emitting diode and the light intensity sensing device. Such information may be used to refine a position the ablation members 42, 44 relative to heart 10. In alternative embodiments, light emitting diodes or other light emitting sources may be incorporated elsewhere on sub-xiphoid ablation clamp 30, including elsewhere on jaw structure 36 including on jaws 38, 40 and on pivot 41, and on neck 34.

Tips 54, 56 of jaws 38, 40 may also include inflatable balloons that may help to separate tissue planes when inflated, which may facilitate advancement of sub-xiphoid ablation clamp 30 or provide space to improve visualization of patient anatomy using line-of-sight or endoscopic visualization, among various possible benefits. Such balloons may be elastic, compliant or non-compliant.

Tips 54, 56 may be configured to be atraumatic, reducing, at least in part, trauma tissue tips 54, 56 create when they are utilized in the body of the patient. In an embodiment, the tips cause no discernable trauma to patient tissue at all. In the illustrated embodiment, tips 54, 56 are bulbous, forming a generally spherical or hemispherical shape. The comparatively large cross section reduces stress on patient tissue into which tips 54, 56 come into contact. In alternative embodiments, tips 54, 56 may be shaped in various other configurations which may be atraumatic to patient tissue. Such embodiments include helical or double-helical shapes, and shapes which are radially flared with respect to first jaw 38 and second jaw 40. Tips 54, 56 and jaws 38 and 40 may be coated with a lubricious coating such as polyacrylamide or polyvinylpyrollidone or other such lubricious material to improve passage through the anatomy. In an embodiment, shown with particularity in FIG. 3d, ablation elements 42, 44 extend onto atraumatic tips 54, 56 in order to increase the size of the resultant lesion which may be created.

Electrodes 58 may be utilized to provide cardiac pacing and cardiac sensing. Electrodes 58 are positioned on jaw 40 relative to ablation element 44 such that when jaw 40 is in contact with cardiac tissue electrodes 58 are distal of heart 10 relative to ablation element 44. When in contact with patient tissue, electrodes 58 may be coupled to a source of pacing energy and deliver pacing energy to the tissue, and a result of the pacing energy on heart 10 noted. A response by heart 10 to the pacing energy may be indicative of an incompleteness of a lesion in the tissue due to the ability of the tissue to conduct energy. Similarly, if electrodes 58 are coupled to a cardiac signal sensing module, electrodes 58 may be utilized in sensing cardiac signals, the continued sensing of which may indicate an incompleteness of a lesion in tissue due to the continued ability of the tissue to conduct electrical signals.

As depicted in FIG. 3a, electrodes 58 are a relief which passes through jaw 40 for purposes of installation of electrodes 58 during manufacture. After manufacture the reliefs may be hermetically sealed. FIG. 3b provides an image of the electrically active contact points of electrodes 58. In the illustrated embodiment, positioning electrodes 58 on jaw 40 may provide a user advantageous visual access of electrodes 58 during ablation procedures. In an alternative embodiment, electrodes 58 are positioned on jaw 38 rather than on jaw 40. In an alternative embodiment, electrodes 58 are positioned on both of jaws 38 and 40.

Using jaw structure 36 with atraumatic tips 54, 56, it may be that no dissections of pericardial reflections 18 are necessary to place sub-xiphoid ablation clamp 30. In various embodiments, sub-xiphoid ablation clamp 30 may be utilized to ablate both the right pulmonary veins and the left pulmonary veins in various ablation procedures.

In various embodiments, jaw structure 36 is configured to rotate about pivot 41 when torque is applied to handle 32 while positioning the ablation jaws. In various of such embodiments, pivot 41 may be selectively locked to limit or prevent rotation of jaw structure 36 relative to handle 32. In such embodiments pivot 41 incorporates a conventional ball and socket hub or similar structure known in the art. Pivot 41 may be rotationally locked utilizing a manually inserted pin, by a control on handle 32, or by other method known in the art.

Figure 4:
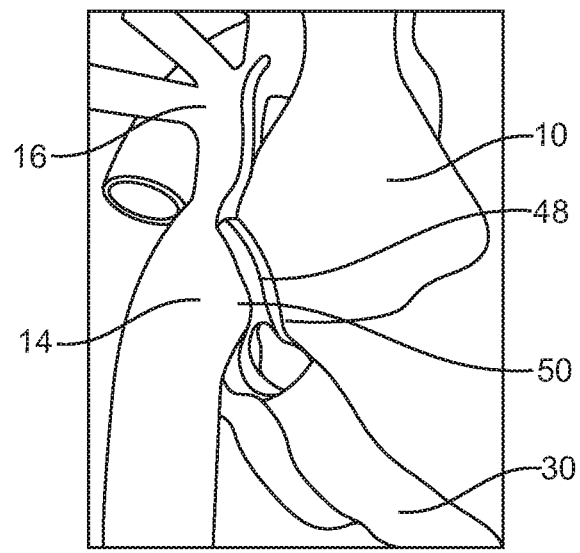
FIG. 4 is an image of the sub-xiphoid ablation clamp in use on a heart.

FIG. 4 shows an example of sub-xiphoid ablation clamp 30 being utilized to ablate right pulmonary veins 16 of heart 10. Sub-xiphoid ablation clamp 30 circumscribes inferior vena cava 14 within void 50 created by relief segments 46 (obscured), 48 in such a way that a real inferior vena cava 14 might not be so occluded as to interfere the delivery of deoxygenated blood to heart 10.

FIG. 5 is a closer view of jaw structure 36 being utilized as in FIG. 4. Ablation members 42, 44 are in contact with the left atrial chamber wall, proximal to both right pulmonary veins 16. Atraumatic tips 54, 56 may be in contact with right pulmonary artery 60 without exerting enough force to cause trauma to tissue. Embodiments in which ports 52 incorporate electrogram recording electrodes are incorporated may be used to determine if the tips 54 have been advanced past the point of contact with the left atrial wall adjacent to the pulmonary veins 16. Embodiments which incorporate electrodes 58 may similarly be utilized to identify a degree of contact with tissue of heart 10. When in contact with the left atrium, a local electrogram may be sensed, while a local electrogram may not be detected when ports 52 are in contact with pulmonary artery 60. Such a sensing system may afford confidence to the user that the device has been properly placed on the intended anatomy.

Figure 6:
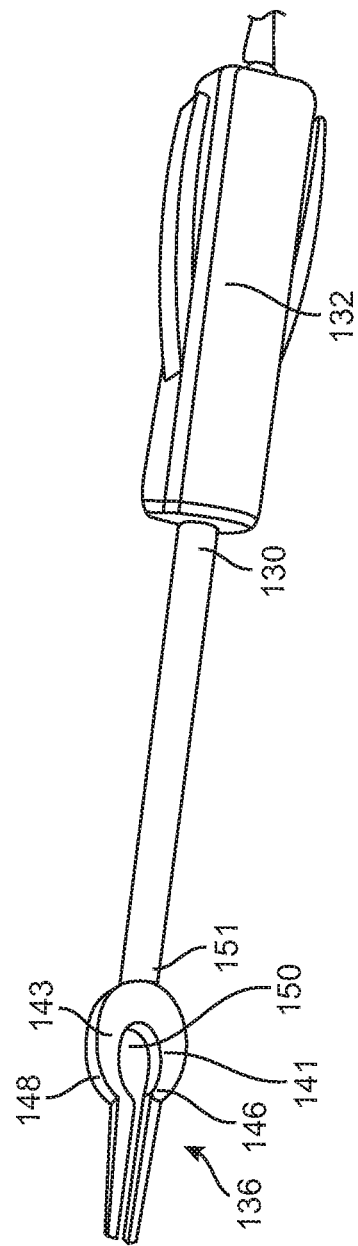
FIG. 6 is a sub-xiphoid ablation clamp with an alternative jaw structure.

FIG. 6 is an embodiment of sub-xiphoid ablation clamp 130 with an alternative jaw structure 136. In contrast to jaw structure 36 illustrated in FIG. 3, relief segments 146, 148 are at least partially proximal of pivots 141, 143 relative to handle 132. Void 150 may be configured to be sufficiently large to circumscribe inferior vena cava 14 or large enough to allow a sufficient portion of the vena cava to remain open to blood flow. In utilizing an alternative embodiment of jaw structure 136, jaw structure 136 may be detachable at neck end 151, and may be replaced by alternative jaw structures, for instance, jaw structure 36. In various embodiments, the dimensions provided by sub-xiphoid ablation clamp 130 are in accordance with the dimensions of sub-xiphoid ablation clamp 30.

Figure 7:
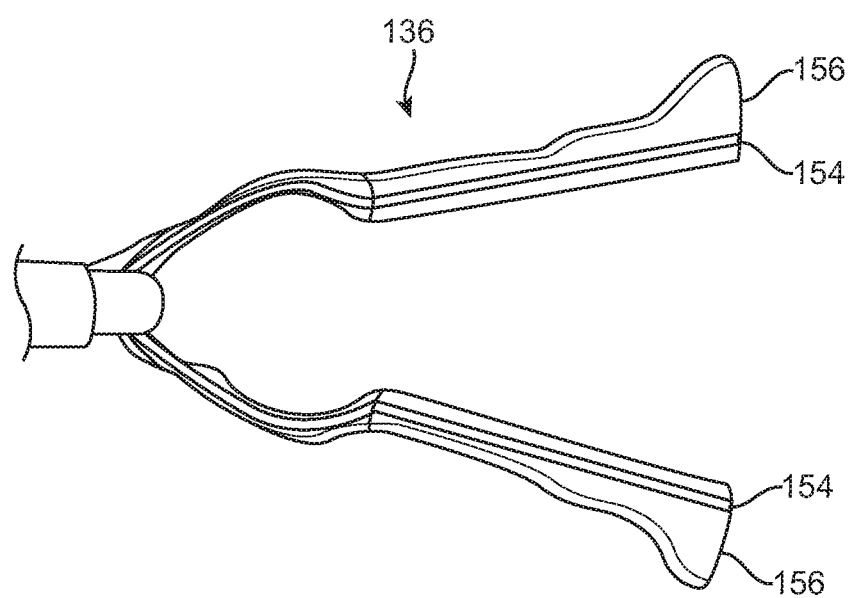
FIG. 7 is a sub-xiphoid ablation clamp with an alternative atraumatic tip.

FIG. 7 illustrates an alternative atraumatic tip 154 of jaw structure 136. Atraumatic tip 154 is configured to be flat, in contrast with bulbous atraumatic tip 54 of sub-xiphoid ablation clamp 30. Flat atraumatic tip 154 may provide an improved ability to dissect patient tissue when necessary and expedient to do so while still being atraumatic during normal use. By providing a front edge 156 which has an edge, albeit a blunt edge, atraumatic tip 154 may be better configured to cut through tissue than bulbous atraumatic tip 54.

Figure 8:
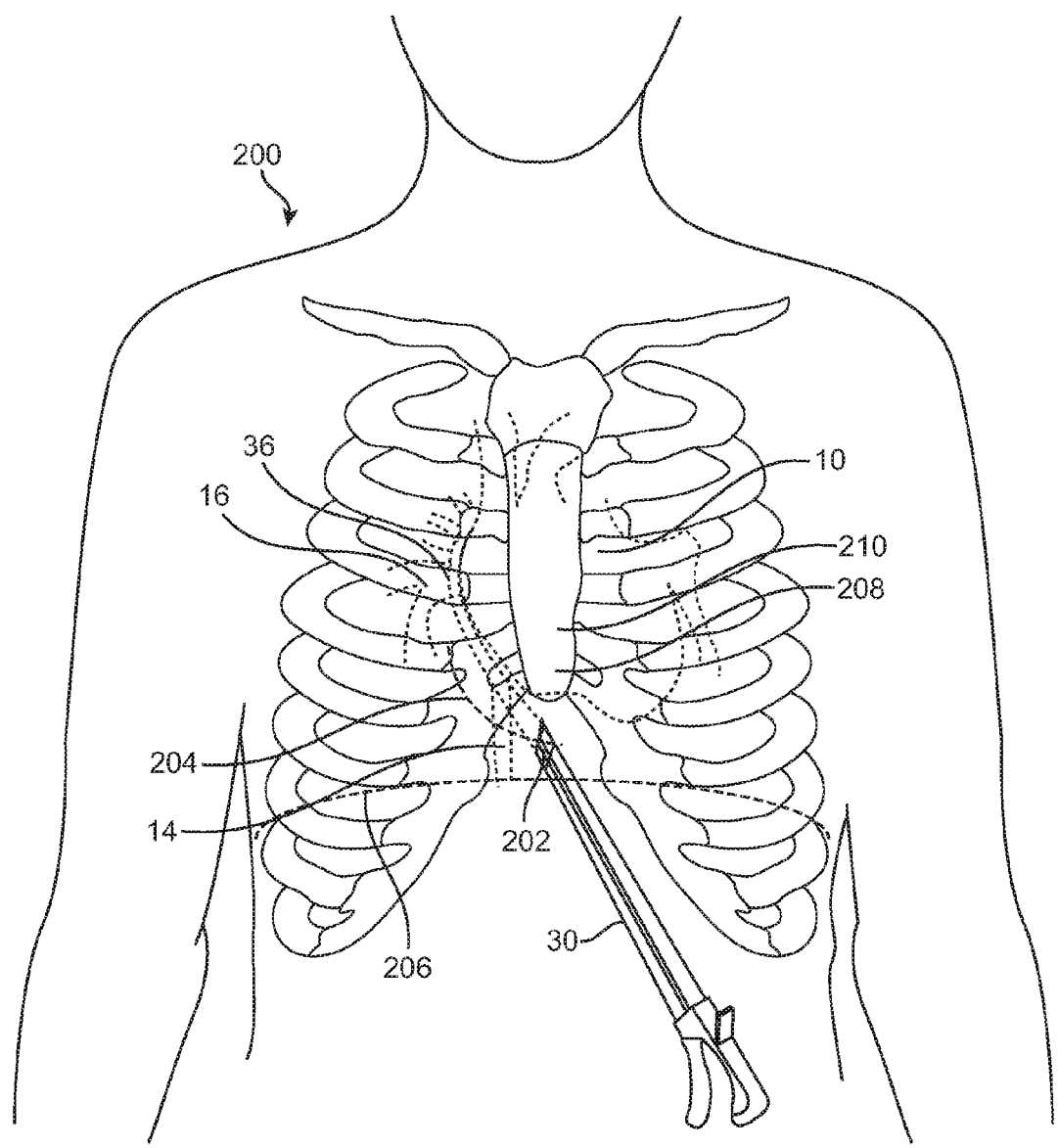
FIG. 8 is a cutaway drawing of a sub-xiphoid ablation clamp in use in a patient.

FIG. 8 is an image of sub-xiphoid ablation clamp 30 in use in a cutaway rendering of patient 200. Preparatory to insertion of sub-xiphoid ablation clamp 30 in patient 200, substernal incision 202 is created in patient 200. Pericardium 204 is cut near diaphragm 206. Subxiphoid process 208 is cut near sternum 210. Once access is provided to heart 10 sub-xiphoid ablation clamp 30 may be inserted for sub-xiphoid use. The most direct path created by substernal incision 202, pericardium 204 and subxiphoid process 208 results in inferior vena cava 14 being generally obstructive of access to right pulmonary veins 16. As illustrated, jaw segment 36 circumscribes inferior vena cava 14 and clamps on right pulmonary veins 16.

Figure 9:
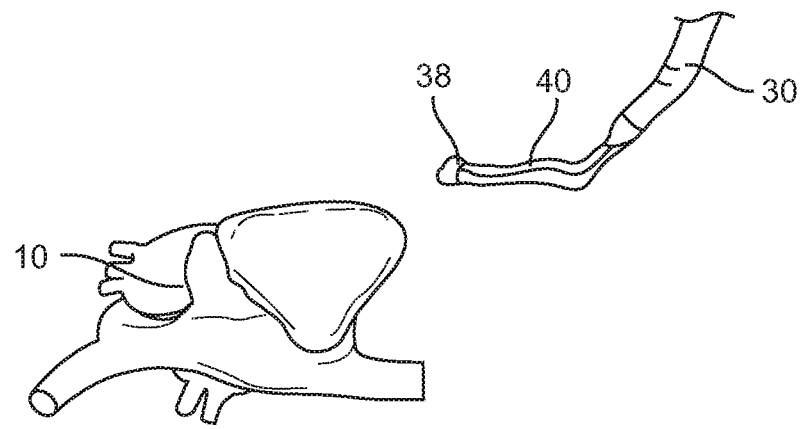
FIGS. 9-17 are a sequence of images of a sub-xiphoid ablation clamp being used within a patient.
Figure 10:
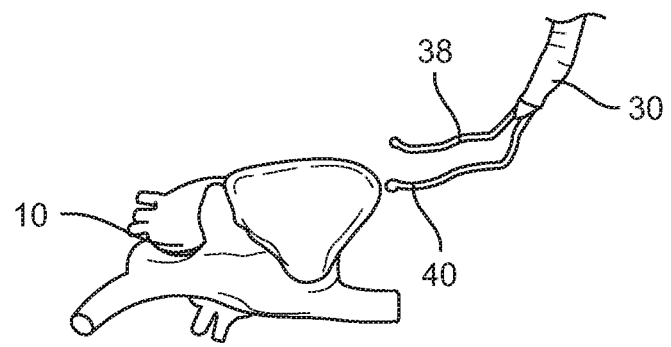
Figure 11:
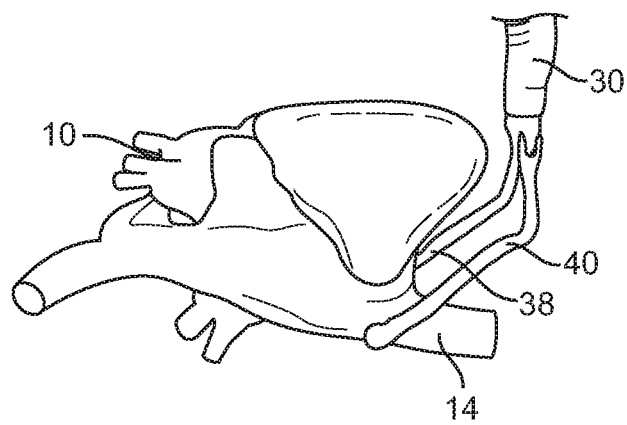
Figure 12:
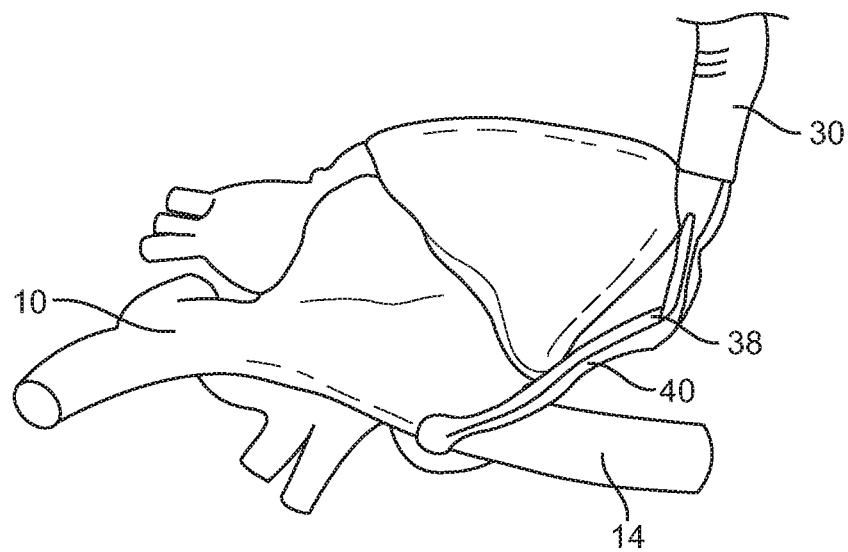
Figure 13:
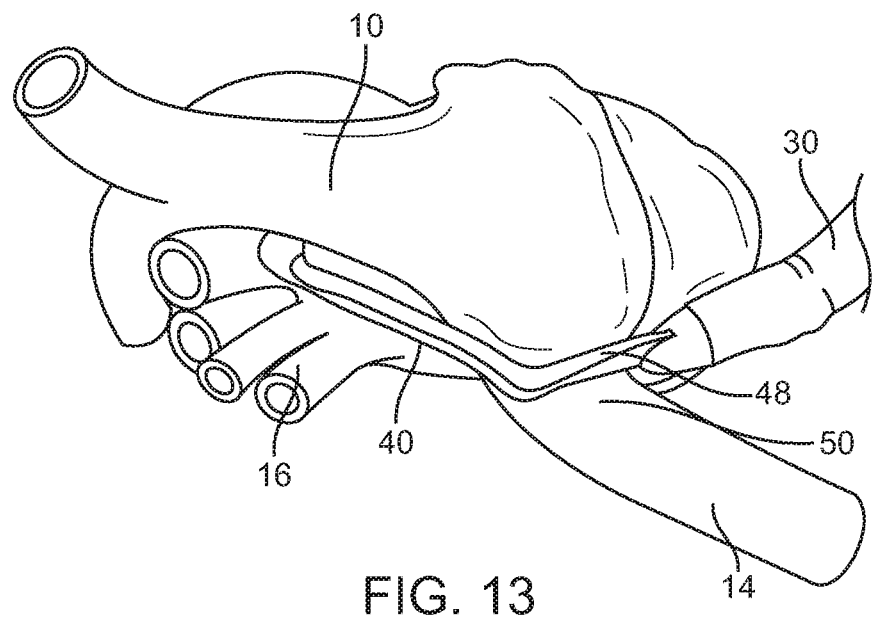
Figure 14:
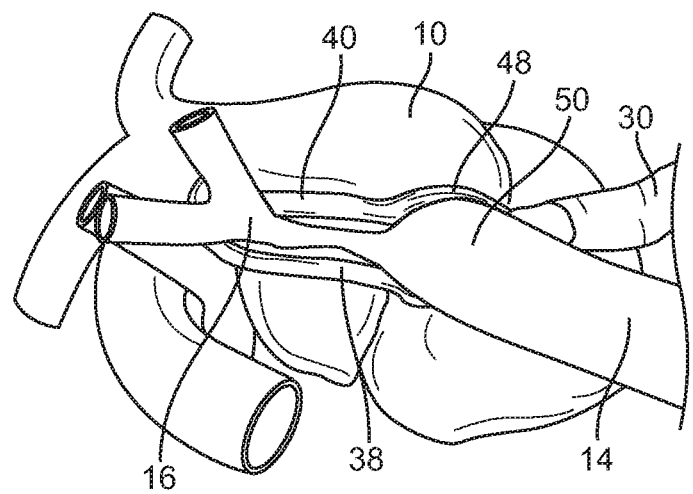
Figure 15:
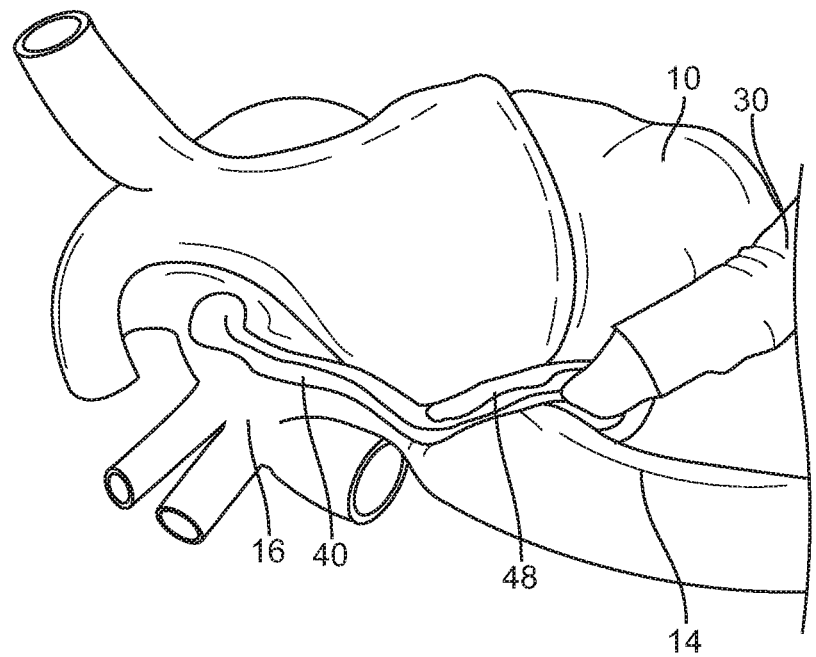
Figure 16:
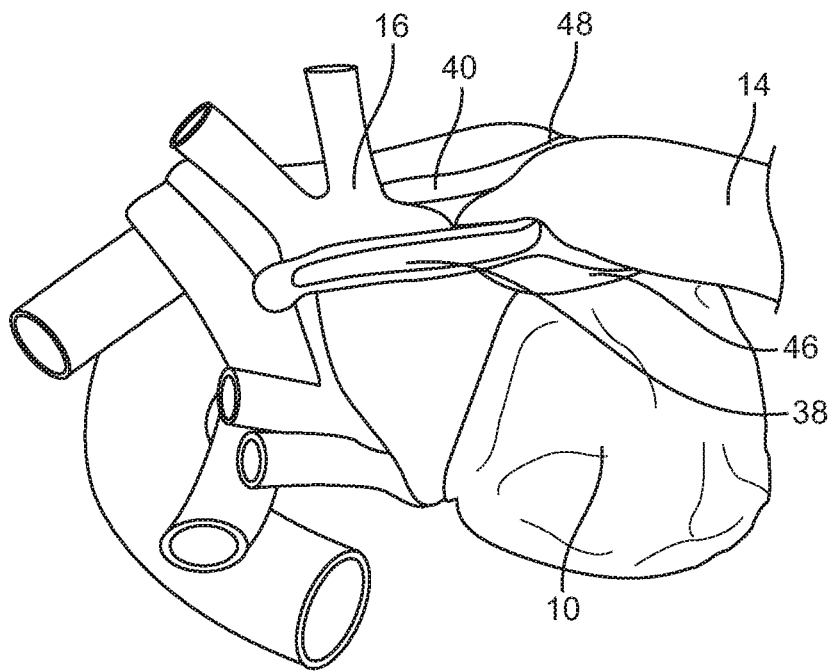
Figure 17:
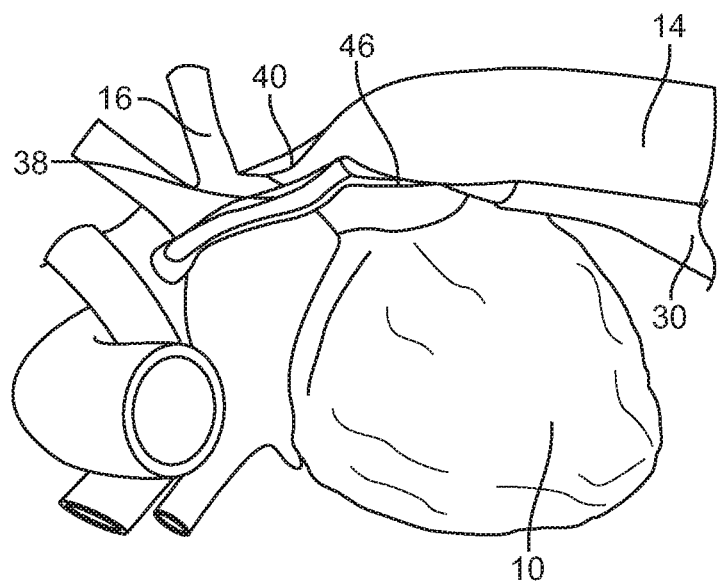

FIGS. 9-17 show a simulation of a sub-xiphoid approach and utilization of sub-xiphoid ablation clamp 30 on a model of heart 10. In FIG. 9 sub-xiphoid ablation clamp 30 approaches heart 10 with jaws 38, 40 closed. In FIG. 10, as sub-xiphoid ablation clamp 30 nears heart 10 jaws 38, 40 are opened. In FIGS. 11 and 12 jaws 38 and 40 pass on opposite sides of inferior vena cava 14. In FIG. 13 inferior vena cava 14 is positioned at least in part within void 50 created by relief segments 46 (obscured), 48 and jaws 38 (obscured), 40 are proximate right pulmonary veins 16. FIGS. 14-17 show various viewpoints of heart 10 and sub-xiphoid ablation clamp 30 after sub-xiphoid ablation clamp 30 has been positioned for ablation of tissue on and around right pulmonary veins 16.

Figure 18:
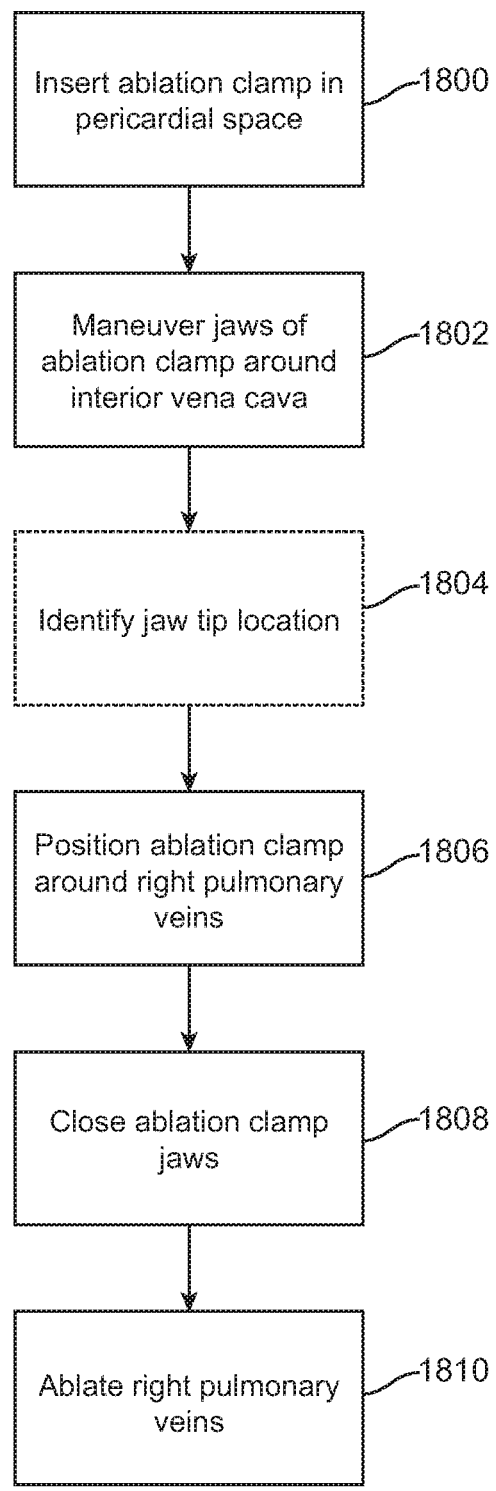
FIG. 18 is a flowchart of using the sub-xiphoid ablation clamp of FIGS. 2a and 2b.

FIG. 18 is a flowchart of a method for ablating right pulmonary veins 16 using sub-xiphoid ablation clamp 30. Jaw structure 36 of sub-xiphoid ablation clamp 30 is inserted (1800) into the pericardial space of the patient proximate heart 10. Jaws 38, 40 are maneuvered (1802) around inferior vena cava 14, so that one jaw 38 passes to one lateral side of inferior vena cava 14 while the other jaw 40 passes to the other lateral side of inferior vena cava and inferior vena cava is generally between jaws 38, 40. Optionally, the user may identify (1804) a location of tips 54, 56 utilizing equipment located in ports 52 such as light emitting diodes, photosensors, cameras, and other equipment disclosed above. Locating the position of ablation elements 42, 44 relative to heart 10 may provide greater assurance that right pulmonary veins 16 will be ablated in contrast to other cardiac structures such as the right pulmonary artery of the patient.

Jaws 38, 40 of sub-xiphoid ablation clamp 30 are positioned (1806) proximate right pulmonary veins 16, with one jaw 38 on one side right pulmonary veins and the other jaw 40 on the opposing side of right pulmonary veins. Jaws 38, 40 are closed (1808), bringing ablation elements 42, 44 into contact with right pulmonary veins 16. Ablation energy is delivered (1810) to right pulmonary veins 16 in order to create the lesion.

Figure 19:
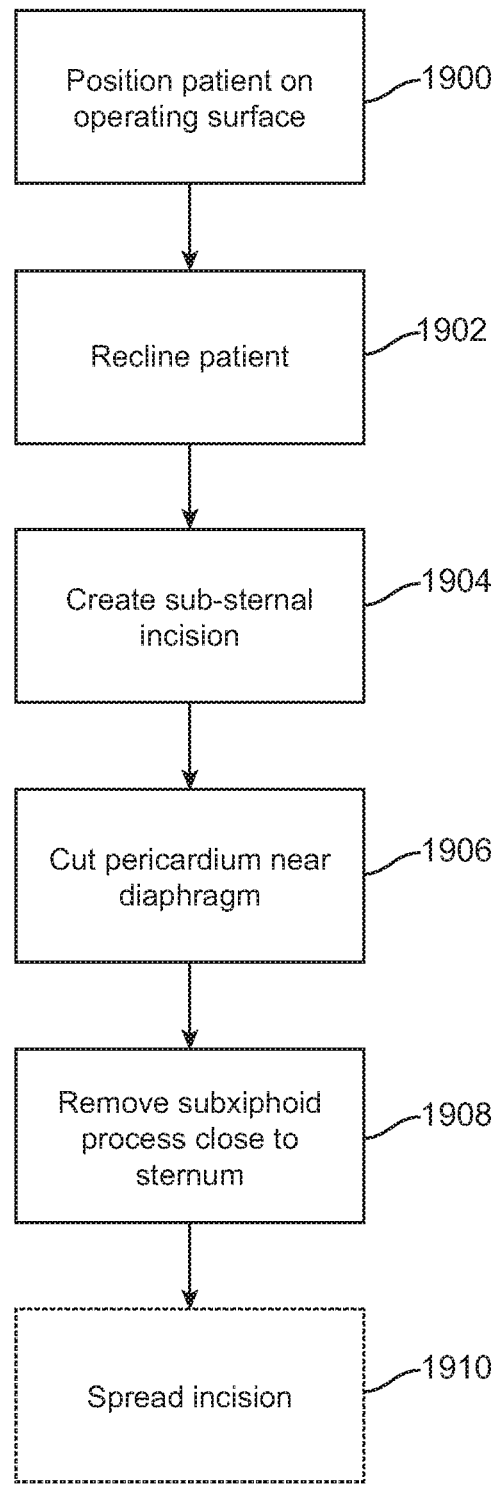
FIG. 19 is a flowchart of inserting the sub-xiphoid ablation clamp of FIGS. 2a and 2b within a patient.

FIG. 19 is a flowchart for a procedure which may be preparatory to implementing the ablation method of FIG. 18. A patient is positioned (1900) on an operating surface. In various embodiments, the operating surface is part of a reclining table, examples of which are well known in the art. The operating surface, and by extension the patient, is reclined (1902) from between approximately 10.0° and approximately 35.0°. In various embodiments the degree of recline is selected in order to give a medical professional a preferred sub-xiphoid angle of approach to heart 10. In an embodiment, the patient is reclined approximately 20.0°.

Sub-xiphoid incision 202 is created (1904) in the skin of the patient, typically starting at the inferior aspect of the sternum and extending inferiorly along the midline. In various embodiments initial sub-xiphoid incision 202 is wide enough to permit introduction of jaw segment 36 and a portion of neck 34 proximate heart 10. In various of such embodiments, jaws 38, 40 are in open position, while in other embodiments jaws 38, 40 are in a closed position. In alternative embodiments, sub-xiphoid incision 202 is not initially large enough to permit introduction of jaw segment 36 and neck 34, and is instead large enough to allow the introduction of cutting devices. In various embodiments, sub-xiphoid incision 202 is from approximately one (1) centimeter in width to approximately 12.0 centimeters in width. In an embodiment sub-xiphoid incision 202 is approximately eight (8) centimeters in length.

After creation of sub-xiphoid incision 202, the pericardium 204 of heart 10 is cut (1906) proximate the diaphragm 206 of the patient to create access to heart 10. Similarly with sub-xiphoid incision 202, the cut in pericardium 204 may be wide enough to permit passage through the cut of jaw segment 36 and a portion of neck 34. As with the creation of sub-xiphoid incision 202, in various embodiments the pericardial cut is large enough to allow jaws 38, 40 to pass through in an open position in some embodiments and in a closed position in other embodiments. The xiphoid process 208 of the patient is then removed (2208) proximate the sternum to improve access. In an embodiment, xiphoid process 208 is removed as close to sternum 210 as may be safely attained. In alternative embodiments, xiphoid process 208 is removed somewhat farther away from sternum 210, albeit still close to sternum 210. Once steps (1906) and (1908) have been performed, sub-xiphoid incision 202 may be spread (1910) if necessary to permit introduction (FIG. 18, 1800) of jaw segment 36 and neck 34.

Thus, embodiments of the invention are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method of sub-xiphoid ablation of a first vessel of a heart of a patient with a sub-xiphoid ablation clamp comprising first and second opposing jaws comprising first and second opposing relief segments being generally co-planar and concave with respect to one another to form a void therebetween and first and second opposing elongate ablation elements positioned along said first and second opposing jaws and distal of said first and second opposing relief segments relative to a handle, respectively, and configured to ablate said first vessel positioned therebetween, wherein said first and second opposing jaws are articulable, comprising the steps of:

approaching said heart with said first and second opposing jaws of said sub-xiphoid ablation clamp from a sub-xiphoid direction;

positioning a second vessel within said void formed by said first and second opposing relief segments and said first vessel between said first and second opposing elongate ablation elements;

clamping said first vessel between said first and second opposing elongate ablation elements while maintaining blood flow through said second vessel, including pivoting said first and second opposing jaws about a common pivot point located inside of said patient and proximal said void;

delivering ablation energy to said first vessel via said first and second opposing elongate ablation elements.

2. The method of claim 1 wherein said first vessel is a right pulmonary vein and said second vessel is an inferior vena cava.

3. The method of claim 1 wherein said sub-xiphoid ablation clamp further comprises an electrode positioned on said sub-xiphoid ablation clamp to contact tissue of said patient when said first and second opposing elongate ablation elements are in contact with said tissue of said patient as part of said step of clamping said first vessel between said first and second opposing elongate ablation elements, and further comprising the step of delivering pacing energy to said heart of said patient to generate a result.

4. The method of claim 3 wherein said delivering ablation energy step is based, at least in part, on said result.

5. The method of claim 1 wherein said sub-xiphoid ablation clamp further comprises an electrode positioned on said sub-xiphoid ablation clamp to contact tissue of said patient when said first and second opposing elongate ablation elements are in contact with said tissue of said patient as part of said step of clamping said first vessel between said first and second opposing elongate ablation elements, and further comprising the step of sensing a cardiac signal from said heart of said patient.

6. The method of claim 5 wherein said delivering ablation energy step is based, at least in part, on said cardiac signal sensed from said heart.

7. The method of claim 1 wherein said sub-xiphoid ablation clamp further comprises an imaging member generating an output, and wherein at least one of said approaching step and positioning step are based, at least in part, on said output.

8. The method of claim 1 wherein said heart has a pericardial reflection, and wherein said pericardial reflection is not dissected.

\* \* \* \* \*